United States Patent
Mariani et al.

(10) Patent No.: US 10,072,303 B2
(45) Date of Patent: Sep. 11, 2018

(54) METHODS AND MATERIALS FOR TREATING ENDOMETRIAL CANCER

(71) Applicant: Mayo Foundation for Medical Education and Research, Rochester, MN (US)

(72) Inventors: Andrea Mariani, Rochester, MN (US); Nicholas Chia, Rochester, MN (US); Marina R. Walther-Antonio, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 15/129,915

(22) PCT Filed: Mar. 27, 2015

(86) PCT No.: PCT/US2015/022963
§ 371 (c)(1),
(2) Date: Sep. 28, 2016

(87) PCT Pub. No.: WO2015/148909
PCT Pub. Date: Oct. 1, 2015

(65) Prior Publication Data
US 2017/0211146 A1 Jul. 27, 2017

Related U.S. Application Data

(60) Provisional application No. 61/971,938, filed on Mar. 28, 2014.

(51) Int. Cl.
*C12Q 1/689* (2018.01)
*C12Q 1/6886* (2018.01)

(52) U.S. Cl.
CPC ............ *C12Q 1/6886* (2013.01); *C12Q 1/689* (2013.01); *C12Q 2600/156* (2013.01); *C12Q 2600/158* (2013.01)

(58) Field of Classification Search
None
See application file for complete search history.

(56) References Cited

U.S. PATENT DOCUMENTS

| | | |
|---|---|---|
| 7,359,802 B1 | 4/2008 | Lewis et al. |
| 7,625,704 B2 | 12/2009 | Fredricks et al. |
| 2007/0178495 A1 | 8/2007 | Fredericks et al. |
| 2011/0104692 A1 | 5/2011 | Rudi et al. |
| 2011/0207622 A1* | 8/2011 | Wong .................. C12Q 1/6886 506/9 |
| 2012/0058094 A1 | 3/2012 | Blaser et al. |
| 2012/0129794 A1 | 5/2012 | Dowd et al. |
| 2013/0059290 A1 | 3/2013 | Armes |
| 2017/0260571 A1 | 9/2017 | Mariani et al. |

FOREIGN PATENT DOCUMENTS

WO WO 2015148909 10/2015

OTHER PUBLICATIONS

Von Gruenigen et al. 2000 (Bacteriology and Treatment of Malodorous Lower Reproductive Tract in Gynecologic cancer patients; Obstetrics & Gynecology; 96(1):23-27); (Year: 2000).*
Walther-Antonio et al. 2016 (Potential contribution of the uterine microbiome in the development of endometrial cancer; Genome Medicine, 8(122): 1-15). (Year: 2016).*
Ahn et al. 2013 (Human Gut Microbiome and Risk for Colorectal Cancer; JNCI 105(24): 1907-1911); (Year: 2013).*
Summanen et al. 2005 (*Porphyromonas somerae* sp. nov., a Pathogen Isolated from Humans and Distinct from *Porphyromonas levii*; Journal of Clinical Microbiology 43(9):4455-4459). (Year: 2005).*
Spiegel et al. 1991 (Bacterial Vaginosis; Clinical Microbiology Reviews 4(4):485-502) (Year: 1991).*
Ahlquist et al., "Next-generation stool DNA test accurately detects colorectal cancer and large adenomas," *Gastroenterology*, Feb. 2012,142(2):248-256; quiz e25-26, Epub Nov. 4, 2011.
Ahn et al., "Human gut microbiome and risk for colorectal cancer," *J Natl Cancer Inst.*, 105(24):1907-1911, Epub Dec. 6, 2013.
Arndt et al., "METAGENassist: a comprehensive web server for comparative metagenomics," *Nucleic Acids Res.*, 40(Web Server issue):W88-W95, Epub May 29, 2012.
Arzese et al., "Detection of resistance factors tetQ and ermF in Prevotel and Porphyromonas isolates from clinical specimens and resident microbiota of humans," *J Antimicrob Chemother*, May 2000, 45(5):577-582.
Arzese et al., "Detection of tetQ and ermF antibiotic resistance genes in Prevotella and Porphyromonas isolates from clinical specimens and resident microbiota of humans," *J Antimicrob Chemother.*, 45(5):577-582, May 2000.
Bansal et al., "The molecular biology of endometrial cancers and the implications for pathogenesis, classification, and targeted therapies," *Cancer Control.*, 16(1):8-13, Jan. 2009.
Barakat et al., "Effect of adjuvant tamoxifen on the endometrium in women with breast cancer: a prospective study using office endometrial biopsy," *J Clin Oncol.*, 18(20):3459-3463, Oct. 15, 2000.
Beral et al., "Endometrial cancer and hormone-replacement therapy in the Million Women Study," *Lancet*, 365(9470):1543-1551, Apr. 30, 2005.
Bogani et al., "Role of pelvic and para-aortic lymphadenectomy in endometrial cancer: current evidence," *J Obstet Gynaecol Res.*, 40(2):301-311, Feb. 2014.
Boggess et al., "A comparative study of 3 surgical methods for hysterectomy with staging for endometrial cancer: robotic assistance, laparoscopy, laparotomy," *Am J Obstet Gynecol.*, 199(4):360. e1-9, Oct. 2008.

(Continued)

*Primary Examiner* — Mary M Lyons
(74) *Attorney, Agent, or Firm* — Fish & Richardson P.C.

(57) ABSTRACT

This document provides methods and materials for treating endometrial cancer. For example, methods and materials for identifying a female mammal as having endometrial cancer and surgically removing at least the uterus of the female are provided.

8 Claims, 4 Drawing Sheets
Specification includes a Sequence Listing.

(56) References Cited

OTHER PUBLICATIONS

Bradley et al., "The emerging role of the intestine in metabolic diseases," *Arch Physiol Biochem.*, 117(3):165-176, Jul. 2011.

Braundmeier et al., "Individualized medicine and the microbiome in reproductive tract," *Front Physiol.*, 6:97, eCollection 2015, Apr. 1, 2015.

Bretelle et al., "High Atopobium vaginae and Gardnerella vaginalis vaginal loads are associated with preterm birth," *Clin Infect Dis.*, 60(6):860-867 Epub Dec. 1, 2014.

Brotman et al., "Association between the vaginal microbiota, menopause status, and signs of vulvovaginal atrophy," *Menopause*, 21(5):450-458, May 2014.

Candela et al., "Maintenance of a healthy trajectory of the intestinal microbiome during aging: a dietary approach," *Mech Ageing Dev.*, 136-137:70-75, Epub Dec. 25, 2013.

Caporaso et al., "QIIME allows analysis of high-throughput community sequencing data," *Nat Methods.*, 7(5):335-336, Epub Apr. 11, 2010.

Carey et al., "Metronidazole to prevent preterm delivery in pregnant women with asymptomatic bacterial vaginosis. National Institute of Child Health and Human Development Network of Maternal-Fetal Medicine Units," *N Engl J Med.*, 342(8):534-540, Feb. 24, 2000.

Castellarin et al., "Fusobacterium nucleatum infection is prevalent in human colorectal carcinoma," *Genome Res.*, 22(2):299-306, Epub Oct. 18, 2011.

Chen et al., "Associating microbiome composition with environmental covariates using generalized UniFrac distances," *Bioinformatics*, 28(16):2106-2113, Epub Jun. 17, 2012.

Chen et al., "Human intestinal lumen and mucosa-associated microbiota in patients with colorectal cancer," *PLoS One*, 7(6):e39743, Epub Jun. 28, 2012.

Cicinelli et al., "Chronic endometritis: correlation among hysteroscopic, histologic, and bacteriologic findings in a prospective trial with 2190 consecutive office hysteroscopies," *Fertil Steril.*, 89(3):677-684, Epub May 25, 2007.

Claros et al., "Differences in distribution and antimicrobial susceptibility of anaerobes isolated from complicated intra-abdominal infections versus diabetic foot infections," Diagn *Microbiol Infect Dis.*, 76(4):546-548, Epub May 30, 2013.

Coussens et al., "Inflammation and cancer," *Nature*, 420(6917):860-867, Dec. 19-26, 2002.

Cowling et al., "Bacterial colonization of the non-pregnant uterus: a study of pre-menopausal abdominal hysterectomy specimens," *Eur J Clin Microbiol Infect Dis.*, 11(2):204-205, Feb. 1992.

De Bandt et al., "Intestinal microbiota in inflammation and insulin resistance: relevance to humans," *Curr Opin Clin Nutr Metab Care*, 14(4):334-340, Jul. 2011.

Donders et al., "Predictive value for preterm birth of abnormal vaginal flora, bacterial vaginosis and aerobic vaginitis during the first trimester of pregnancy," *BJOG.*, 116(10):1315-1324, Epub Jun. 17, 2009.

Dossus et al., "Obesity, inflammatory markers, and endometrial cancer risk: a prospective case-control study," *Endocr Relat Cancer*, 17(4):1007-1019, Oct. 29, 2010.

Durmaz et al., "Evaluation of culture results of specimens from patients with suspected anaerobic infection," *The New Microbiol.*, 22(2), Apr. 1999, 1 page, Abstract Only.

Fader et al., "Endometrial cancer and obesity: epidemiology, biomarkers, prevention and survivorship," *Gynecol Oncol.*, 114(1):121-127, Epub Apr. 29, 2009.

Farage et al., "Lifetime changes in the vulva and vagina," *Arch Gynecol Obstet.*, 273(4):195-202, Epub Oct. 6, 2005.

Fardini et al., "Transmission of diverse oral bacteria to murine placenta: evidence for the oral microbiome as a potential source of intrauterine infection," *Infect Immun.*, 78(4):1789-1796, Epub Feb. 1, 2010.

Ferris et al., "Association of Atopobium vaginae, a recently described metronidazole resistant anaerobe, with bacterial vaginosis," *BMC Infect Dis.*, 4:5, Feb. 13, 2004, 8 pages.

Flores et al., "Fecal microbial determinants of fecal and systemic estrogens and estrogen metabolites: a cross-sectional study," *J Transl Med.*, 10:253, Dec. 21, 2012.

Fredricks et al., "Molecular identification of bacteria associated with bacterial vaginosis," *N Engl J Med.*, 353(18):1899-1911, Nov. 3, 2005.

Fredricks et al., "Targeted PCR for detection of vaginal bacteria associated with bacterial vaginosis," *J Clin Microbiol.*, 45(10):3270-3276, Epub Aug. 8, 2007.

Freedman, "Vaginal pH, estrogen and genital atrophy," *Menopause Management*, 17(4):9-13, 2008.

Friberg et al., "Diabetes mellitus and risk of endometrial cancer: a meta-analysis," *Diabetologia*, 50(7):1365-1374, Epub May 3, 2007.

Funkhouser et al., "Mom knows best: the universality of maternal microbial transmission," *PLoS Biol.*, 11(8):e1001631, Epub Aug. 20, 2013.

Future II Study Group, "Quadrivalent vaccine against human papillomavirus to prevent high-grade cervical lesions," *N Engl J Med.*, 356:1915-1927, May 10, 2007.

Gajer et al., "Temporal dynamics of the human vaginal microbiota," *Sci Transl Med.*, 4(132):132ra52, May 2, 2012.

Gerber et al., "Effects of adjuvant tamoxifen on the endometrium in postmenopausal women with breast cancer: a prospective long-term study using transvaginal ultrasound," *J Clin Oncol.*, 18(20):3464-3470, Oct. 15, 2000.

Giatromanolaki et al., "Human papillomavirus in endometrial adenocarcinomas: infectious agent or a mere 'passenger'?" *Infect Dis Obstet Gynecol.*, 2007:60549, 2007, 4 pages.

Goodman et al., "Postmenopausal uterine bleeding," Last Updated 2017, Retrieved on Jan. 24, 2017 from http://www.uptodate.com/contents/postmenopausal-uterine-bleeding?source=see_link, 7 pages.

Goswami et al., "Inflammation: its role and interplay in the development of cancer, with special focus on gynecological malignancies," *Int J Gynecol Cancer*, 18(4):591-599, Epub Oct. 18, 2007.

Grady et al., "Hormone replacement therapy and endometrial cancer: are current regimens safe?" *J Natl Cancer Inst.*, 89(15):1088-1089, Aug. 1997.

Hampel et al., "Definition of overactive bladder and epidemiology of urinary incontinence," *Urology*, 50(6A Suppl):4-14; discussion 15-7, Dec. 1997.

Hampel et al., "Screening for Lynch syndrome (hereditary nonpolyposis colorectal cancer) among endometrial cancer patients," *Cancer Res.*, 66(15):7810-7817, Aug. 1, 2006.

Harmon, "Body Count: Taking Stock of All the Bugs That Call Humans Home," *Scientific American*, 13, Jun. 2012.

Harris et al., "Research electronic data capture (REDCap)—A metadata-driven methodology and workflow process for providing translational research informatics support," *J Biomed Inform*, 42(2):377-381, Epub Sep. 30, 2008.

Hillier et al., "Association between bacterial vaginosis and preterm delivery of a low-birth-weight infant. The Vaginal Infections and Prematurity Study Group," *N Engl J Med.*, 333(26):1737-1742, Dec. 28, 1995.

Horz et al., "Synergistes group organisms of human origin," *J Clin Microbiol.*, 44(8):2914-2920, Aug. 2006.

International Preliminary Report on Patentability for PCT/US2015/022963, dated Oct. 13, 2016, 11 pages.

International Search Report and Written Opinion for PCT/US2015/022963, dated Jul. 8, 2015, 20 pages.

Jabbour et al., "Inflammatory pathways in female reproductive health and disease," *Reproduction*, 138(6):903-919, Epub Sep. 30, 2009.

Kacerovsky et al., "Amniotic fluid protein profiles of intraamniotic inflammatory response to *Ureaplasma* spp. and other bacteria," *PLoS One*, 8(3):e60399, Epub Mar. 26, 2013.

Kaunitz et al., "Approach to abnormal uterine bleeding in nonpregnant reproductive-age women," Topic 3263 Version 17.0, Last Updated Oct. 13, 2016, Retrieved on Dec. 12, 2016 from http://www.uptodate.com/contents/approach-to-abnormal-uterine-bleeding-in-nonpregnant-reproductive-age-women.

Kim et al., "Heterogeneity of vaginal microbial communities within individuals," *J Clin Microbiol.*, 47(4):1181-1189, Epub Jan. 21, 2009.

(56) References Cited

OTHER PUBLICATIONS

King et al., "Succinate dehydrogenase and fumarate hydratase: linking mitochondrial dysfunction and cancer," *Oncogene*, 25(34):4675-4682, Aug. 7, 2006.
Kolata, "In Good Health? Thank Your 100 Trillion Bacteria," The New York Times, p. A24, Jun. 14, 2012, 5 pages.
Kong et al., "Temporal shifts in the skin microbiome associated with disease flares and treatment in children with atopic dermatitis," *Genome Res.*, 22(5):850-859, Epub Feb. 6, 2012.
Koren et al., "Host remodeling of the gut microbiome and metabolic changes during pregnancy," *Cell*, 150(3):470-480, Aug. 3, 2012.
Kostic et al., "Genomic analysis identifies association of Fusobacterium with colorectal carcinoma," *Genome Res.*, 22(2):292-298, Epub Oct. 18, 2011.
Kwon et al., "Testing women with endometrial cancer to detect Lynch syndrome," *J Clin Oncol.*, 29(16):2247-2252, Epub May 2, 2011.
Lampe, "The Human Microbiome Project: getting to the guts of the matter in cancer epidemiology," *Cancer Epidemiol Biomarkers Prev.*, 17(10):2523-2524, Oct. 2008.
Lancaster et al., "Society of Gynecologic Oncologists Education Committee statement on risk assessment for inherited gynecologic cancer predispositions," *Gynecol Oncol.*, 107(2):159-162, Nov. 2007.
Larsen et al., "Gut microbiota in human adults with type 2 diabetes differs from non-diabetic adults," *PLoS One*, 5(2):e9085, Feb. 5, 2010.
León et al., "Detection of Porphyromonas gingivalis in the amniotic fluid in pregnant women with a diagnosis of threatened premature labor," *J Periodontol.*, 78(7):1249-1255, Jul. 2007.
Lewis et al., "Cancer risk in patients with inflammatory bowel disease," *Gastroenterol Clin North Am.*, 28(2):459-477, Jun. 1999.
Love et al., "Investigation of endometrial abnormalities in asymptomatic women treated with tamoxifen and an evaluation of the role of endometrial screening," *J Clin Oncol.*, 17(7):2050-2054, Jul. 1999.
Marchandin et al., "Phylogeny, diversity and host specialization in the phylum Synergistetes with emphasis on strains and clones of human origin," *Res Microbiol.*, 161(2):91-100, Epub Jan. 15, 2010.
Marconi et al., "Correlation of atopobium vaginae amount with bacterial vaginosis markers," *J Low Genit Tract Dis.*, 16(2):127-132, Apr. 2012.
Markle et al., "Sex differences in the gut microbiome drive hormone-dependent regulation of autoimmunity," *Science*, 339(6123):1084-1088, Epub Jan. 17, 2013.
McArdle et al., "Fitting multivariate models to community data: a comment on distance-based redundancy analysis," *Ecology*, 82(1):290-297, Jan. 1, 2001.
McCook, "The vagina catalogues," *Nat Med.*, 17(7):765-767, Jul. 7, 2011.
Menard et al., "High vaginal concentrations of Atopobium vaginae and Gardnerella vaginalis in women undergoing preterm labor," *Obstet Gynecol.*, 115(1):134-140, Jan. 2010.
Messier et al., "Comparison of swabbing and biopsy for studying the flora of the bovine uterus," *Can Vet J.*, 25(7):283-288, Jul. 1984.
Meyerson et al., "Advances in understanding cancer genomes through second-generation sequencing," *Nat Rev Genet.*, 11(10):685-696, Oct. 2010.
Modugno et al., "Inflammation and endometrial cancer: a hypothesis," *Cancer Epidemiol Biomarkers Prev.*, 14(12):2840-2847, Dec. 2005.
Møller et al., "Sterility of the uterine cavity," *Acta Obstet Gynecol Scand.*, 74(3):216-219, Mar. 1995.
Murta et al., "Relation between vaginal and endocervical pH in pre- and post-menopausal women," *Arch Gynecol Obstet.*, 272(3):211-213, Epub Apr. 19, 2005.
NCI SEER Stat Fact Sheets: Endometrial Cancer: http://seer.cancer.gov/statfacts/html/corp.html, retrieved Feb. 22, 2015, 9 pages.

Nieboer et al., "Surgical approach to hysterectomy for benign gynaecological disease," *Cochrane Database Syst Rev.*, (3):CD003677, Jul. 8, 2009.
Nomura et al., "Helicobacter pylori infection and gastric carcinoma among Japanese Americans in Hawaii," *N Engl J Med.*, 325(16):1132-1136, Oct. 17, 1991.
Oh et al., "The association of uterine cervical microbiota with an increased risk for cervical intraepithelial neoplasia in Korea," *Clin Microbiol Infect.*, 21(7):674.e1-9, Epub Mar. 6, 2015.
Parsonnet et al., "Helicobacter pylori infection and the risk of gastric carcinoma," *N Engl J Med.*, 325(16):1127-1131, Oct. 17, 1991.
Parsonnet et al., "Helicobacter pylori infection in intestinal- and diffuse-type gastric adenocarcinomas," *J Natl Cancer Inst.*, 83(9):640-643, May 1, 1991.
Peng et al., "Microbial diversity in uterus of healthy and metritic postpartum Holstein dairy cows," *Folia Microbiol (Praha).*, 58(6):593-600, Epub Apr. 14, 2013.
Polk et al., "Helicobacter pylori: gastric cancer and beyond," *Nat Rev Cancer.*, 10(6):403-414, Jun. 2010.
Precision™ Stool Collector, Vendor Item: 2450SA, © 2015, Retrieved on Dec. 8, 2016, Retrieved from http://products.covidien.com/pages.aspx?page=ProductDetail&id=76679&cat=Collection.
Ravel et al., "Vaginal microbiome of reproductive-age women," *Proc Natl Acad Sci U S A.*, 108 Suppl 1:4680-4687, Epub Jun. 3, 2010.
Roland et al., "The benefits of a gynecologic oncologist: a pattern of care study for endometrial cancer treatment," *Gynecol Oncol.*, 93(1):125-130, Apr. 2004.
Romero et al., "The composition and stability of the vaginal microbiota of normal pregnant women is different from that of non-pregnant women," *Microbiome.*, 2:4, 2014, 19 pages.
Salamonsen et al., "Endometrial leukocytes and menstruation," *Hum Reprod Update*, 6(1):16-27, Jan.-Feb. 2000.
Santos et al., "Diversity and succession of bacterial communities in the uterine fluid of postpartum metritic, endometritic and healthy dairy cows," *PLoS One*, 7(12):e53048. Epub Dec. 27, 2012.
Sipos et al., "Robust computational analysis of rRNA hypervariable tag datasets," *PLoS One*, 5(12):e15220, Dec. 31, 2010.
Smith et al., "American Cancer Society guidelines for the early detection of cancer: update of early detection guidelines for prostate, colorectal, and endometrial cancers. Also: update 2001—testing for early lung cancer detection," *CA Cancer J Clin.*, 51(1):38-75; quiz 77-80, Jan.-Feb. 2001.
Smith et al., "The cervical microbiome over 7 years and a comparison of methodologies for its characterization," *PLoS One*, 7(7):e40425, Epub Jul. 9, 2012.
Subbaramaiah et al., "Cyclooxygenase-2 transcription is regulated by human papillomavirus 16 E6 and E7 oncoproteins: evidence of a corepressor/coactivator exchange," *Cancer Res.*, 67(8):3976-3985, Apr. 15, 2007.
Summanen et al., "*Porphyromonas somerae* sp. nov., a pathogen isolated from humans and distinct from *Porphyromonas levii*," *J Clin Microbiol.*, 43(9):4455-4459, Sep. 2005.
Svenstrup et al., "Mycoplasma genitalium attaches to human spermatozoa," *Hum Reprod.*, 18(10):2103-2109, Oct. 2003.
Swidsinski et al., "Adherent biofilms in bacterial vaginosis," *Obstet Gynecol.*, 106(5 Pt 1):1013-1023, Nov. 2005.
Sze et al., "The lung tissue microbiome in chronic obstructive pulmonary disease," *Am J Respir Crit Care Med.*, 185(10):1073-1080, Epub Mar. 15, 2012.
Talley et al., "Gastric adenocarcinoma and Helicobacter pylori infection," *J Natl Cancer Inst.*, 83(23):1734-1739, Dec. 4, 1991.
Torres et al., "Risk factors for developing endometrial cancer after benign endometrial sampling," *Obstet Gynecol.*, 120(5):998-1004, Nov. 2012.
Tujula et al., "A CARD-FISH protocol for the identification and enumeration of epiphytic bacteria on marine algae," *J Microbiol Methods*, 65(3):604-607, Epub Oct. 10, 2005.
Turnbaugh et al., "An obesity-associated gut microbiome with increased capacity for energy harvest," *Nature*, 444(7122):1027-1031, Dec. 21, 2006.

(56) References Cited

OTHER PUBLICATIONS

Turnbaugh et al., "The human microbiome project: exploring the microbial part of ourselves in a changing world," *Nature*, 449(7164):804-810, Oct. 18, 2007.
Verstraelen et al., "Characterisation of the human uterine microbiome in non-pregnant women through deep sequencing of the V1-2 region of the 16S rRNA gene," *PeerJ.*, 4:e1602, eCollection 2016, Jan. 19, 2016.
Von Gruenigen et al., "Bacteriology and treatment of malodorous lower reproductive tract in gynecologic cancer patients," *Obstet Gynecol.*, 96(1):23-27, Jul. 2000.
Walther-Antonio et al., "Potential Contribution of the Uterine Microbiome in the Development of Endometrial Cancer ," *Genome Medicine*, 8:122, Received: May 31, 2016 Accepted: Oct. 13, 2016, 15 pages.
Walther-António et al., "Pregnancy's stronghold on the vaginal microbiome," *PLoS One*, 9(6):e98514, eCollection 2014, Jun. 4, 2014.
White et al., "The vaginal microbiome in health and disease," *Trends Endocrinol Metab.*, 22(10):389-393, Epub Jul. 13, 2011.
Witkin et al., "Bacterial flora of the female genital tract: function and immune regulation," *Best Pract Res Clin Obstet Gynaecol.*, 21(3):347-354, Epub Jan. 9, 2007.
Wolfe et al., "Evidence of uncultivated bacteria in the adult female bladder," *J Clin Microbiol.*, 50(4):1376-1383, Epub Jan. 25, 2012.
Wong et al., "Helicobacter pylori eradication to prevent gastric cancer in a high-risk region of China: a randomized controlled trial," *JAMA*, 291(2):187-194, Jan. 14, 2004.
Yang et al., "Inflammation and intestinal metaplasia of the distal esophagus are associated with alterations in the microbiome," *Gastroenterology*, 137(2):588-597, Epub Apr. 23, 2009.
Ye, "Identification and Quantification of Abundant Species from Pyrosequences of 16S rRNA by Consensus Alignment," *Proceedings (IEEE Int Conf Bioinformatics Biomed).*, 2010:153-157, Feb. 4, 2011.
Zanssen et al., "Mitochondrial DNA mutations in cancer," *PLoS Med.*, 2(11):e401, 1082-1084, Epub Nov. 29, 2005.
zur Hausen, "Papillomaviruses in the causation of human cancers—a brief historical account," *Virology*, 384(2):260-265, Epub Jan. 8, 2009.

\* cited by examiner

METHODS AND MATERIALS FOR TREATING ENDOMETRIAL CANCER

CROSS REFERENCE TO RELATED APPLICATIONS

This application is a National Stage application under 35 U.S.C. § 371 of International Application No. PCT/US2015/022963, having an International Filing Date of Mar. 27, 2015, which claims the benefit of U.S. Provisional Ser. No. 61/971,938 filed Mar. 28, 2014. This disclosure of the prior application is considered part of (and is incorporated by reference in) the disclosure of this application.

BACKGROUND

1. Technical Field

This document relates to methods and materials involved in treating endometrial cancer. For example, this document provides methods and materials for identifying a female mammal as having endometrial cancer and surgically removing at least the uterus of the female.

2. Background Information

Endometrial cancer is the most common gynecologic cancer currently afflicting an estimated 600,000 women in the U.S. alone, with 49,000 new cases identified and 8,000 deaths in 2013. Genetic risk factors, such as hereditary non-polyposis colorectal cancer, explain less than 5% of all endometrial cancer cases (Lancaster et al., *Gynecol. Oncol.*, 107(2):159-162 (2007) and Kwon et al., *J. Clin. Oncol.*, 29(16):2247-2252 (2011)). Multiple non-genetic risk factors for endometrial cancer exist. These risk factors can be broadly categorized into those linked to hormonal changes, such as obesity and hormone therapy, and those linked to chronic inflammation, such as diabetes and aging (Smith et al., *Cancer J. Clinicians*, 51(1):38-75 (2001)).

SUMMARY

This document provides methods and materials for treating endometrial cancer. For example, this document provides methods and materials for identifying a female mammal as having endometrial cancer and surgically removing at least the uterus of the female.

As described herein, a female mammal can be identified as having endometrial cancer at an early stage based at least in part on the presence of a *Porphyromonas* species in the upper reproductive tract and/or based at least in part on the presence of an elevated level of bacteria of a *Porphyromonas* species in the lower reproductive tract. In some cases, endometrial biopsies, dilatation and curettage procedures, transvaginal ultrasound examinations, or combinations thereof can be used to confirm that a female has endometrial cancer. Once identified as having endometrial cancer as described herein, at least the uterus of the female mammal can be surgically removed. For example, a female mammal identified as having endometrial cancer as described herein can be treated by performing a total hysterectomy (e.g., a vaginal hysterectomy, an abdominal hysterectomy, a total laparoscopic hysterectomy, a total hysterectomy with lateral or bilateral salpingo-oophorectomy, or a radical hysterectomy). In some cases, a female mammal identified as having endometrial cancer as described herein can be treated using radiation therapy (e.g., high-energy x-ray therapy), chemotherapy (e.g., paclitaxel, carboplatin, doxorubicin, and/or cisplatin therapy), or hormone therapy (e.g., tamoxifen, goserelin, leuprolide, exemestane, anastrozole, and/or letrozole therapy) in combination with or in place of surgery.

In general, one aspect of this document features a method for treating a female mammal having endometrial cancer. The method comprises, or consists essentially of, (a) identifying the mammal as having a *Porphyromonas* species within the upper reproductive tract of the mammal or as having an elevated level of the species within the lower reproductive tract of the mammal, wherein the species is *Porphyromonas somerae* or a species having 16S rRNA that is greater than 98 percent identical to a 16 rRNA sequence of *Porphyromonas somerae*, and (b) removing at least the uterus of the mammal. The mammal can be a human. The method can comprise identifying the mammal as having the species within the upper reproductive tract of the mammal. The method can comprise identifying the mammal as having the elevated level of the species within the lower reproductive tract of the mammal. The *Porphyromonas* species can be *Porphyromonas somerae*. The *Porphyromonas* species can be the species having 16S rRNA that is greater than 98 percent identical to a 16 rRNA sequence of *Porphyromonas somerae*. The *Porphyromonas* species can be the species having 16S rRNA that is greater than 98.5 percent identical to a 16 rRNA sequence of *Porphyromonas somerae*.

In another aspect, this document features a method for identifying a female mammal as having endometrial cancer. The method comprises, or consists essentially of, (a) detecting the presence of a *Porphyromonas* species within the upper reproductive tract of the mammal or the presence of an elevated level of the species within the lower reproductive tract of the mammal, wherein the species is *Porphyromonas somerae* or a species having 16S rRNA that is greater than 98 percent identical to a 16 rRNA sequence of *Porphyromonas somerae*, and (b) classifying the mammal as having endometrial cancer. The mammal can be a human. The method can comprise detecting the presence of the species within the upper reproductive tract of the mammal. The method can comprise detecting the presence of the elevated level of the species within the lower reproductive tract of the mammal. The *Porphyromonas* species can be *Porphyromonas somerae*. The *Porphyromonas* species can be a species having 16S rRNA that is greater than 98 percent identical to a 16 rRNA sequence of *Porphyromonas somerae*. The *Porphyromonas* species can be a species having 16S rRNA that is greater than 98.5 percent identical to a 16 rRNA sequence of *Porphyromonas somerae*.

In another aspect, this document features a method for identifying a female mammal as having endometrial cancer. The method comprises, or consists essentially of, (a) obtaining a sample from the upper reproductive tract of the mammal, (b) extracting nucleic acid from the sample, (c) contacting the extracted nucleic acid with a primer pair capable of amplifying nucleic acid of a *Porphyromonas* species to form a mixture, (d) performing a polymerase chain reaction with the mixture to obtain an amplification product, (e) analyzing the amplification product to detect the presence of nucleic acid of a *Porphyromonas* species, wherein the species is *Porphyromonas somerae* or a species having 16S rRNA that is greater than 98 percent identical to a 16 rRNA sequence of *Porphyromonas somerae*, and (f) classifying the mammal as having endometrial cancer. The mammal can be a human. The *Porphyromonas* species can be *Porphyromonas somerae*. The *Porphyromonas* species can be a species having 16S rRNA that is greater than 98 percent identical to a 16 rRNA sequence of *Porphyromonas somerae*. The *Porphyromonas* species can be a species having 16S rRNA that is greater than 98.5 percent identical to a 16 rRNA sequence of *Porphyromonas* somerae.

In another aspect, this document features a method for identifying a female mammal as having endometrial cancer. The method comprises, or consists essentially of, (a) obtaining a sample from the lower reproductive tract of the mammal, (b) extracting nucleic acid from the sample, (c) contacting the extracted nucleic acid with a primer pair capable of amplifying nucleic acid of a *Porphyromonas* species to form a mixture, (d) performing a polymerase chain reaction with the mixture to obtain an amplification product, (e) analyzing the amplification product to detect an elevated level of nucleic acid of a *Porphyromonas* species, wherein the species is *Porphyromonas somerae* or a species having 16S rRNA that is greater than 98 percent identical to a 16 rRNA sequence of *Porphyromonas somerae*, and (f) classifying the mammal as having endometrial cancer. The mammal can be a human. The *Porphyromonas* species can be *Porphyromonas somerae*. The *Porphyromonas* species can be a species having 16S rRNA that is greater than 98 percent identical to a 16 rRNA sequence of *Porphyromonas somerae*. The *Porphyromonas* species can be a species having 16S rRNA that is greater than 98.5 percent identical to a 16 rRNA sequence of *Porphyromonas* somerae.

In another aspect, this document features a method for treating a female mammal having endometrial cancer or likely to develop endometrial cancer. The method comprises, or consists essentially of, (a) identifying the mammal as having a *Porphyromonas* species within the upper reproductive tract of the mammal or as having an elevated level of the species within the lower reproductive tract of the mammal, wherein the species is *Porphyromonas somerae* or a species having 16S rRNA that is greater than 98 percent identical to a 16 rRNA sequence of *Porphyromonas somerae*, and (b) administering an antibiotic to the mammal to reduce the number of the species within the mammal. The mammal can be a human. The method can comprise identifying the mammal as having the species within the upper reproductive tract of the mammal. The method can comprise identifying the mammal as having the elevated level of the species within the lower reproductive tract of the mammal. The *Porphyromonas* species can be *Porphyromonas somerae*. The *Porphyromonas* species can be the species having 16S rRNA that is greater than 98 percent identical to a 16 rRNA sequence of *Porphyromonas somerae*. The *Porphyromonas* species can be the species having 16S rRNA that is greater than 98.5 percent identical to a 16 rRNA sequence of *Porphyromonas* somerae. The antibiotic can be benzylpenicillin, tetracycline, amoxicillin, ampicillin, ticarcillin, piperacillin, cephalothin, cefuroxime, cefotaxime, cefoxitin, imipenem erythromycin, cefamandole, cephaloridine, oleandomycin, metronidazole, spiramycin, or clindamycin.

In another aspect, this document features a method for identifying a female mammal as having endometrial cancer. The method comprises, or consists essentially of, (a) contacting a sample from the mammal with a FISH probe during a FISH technique to detect the presence of a *Porphyromonas* species within the upper reproductive tract of the mammal or the presence of an elevated level of the species within the lower reproductive tract of the mammal, wherein the species is *Porphyromonas somerae* or a species having 16S rRNA that is greater than 98 percent identical to a 16 rRNA sequence of *Porphyromonas somerae*, and (b) classifying the mammal as having endometrial cancer. The mammal can be a human. The method can comprise detecting the presence of the species within the upper reproductive tract of the mammal. The method can comprise detecting the presence of the elevated level of the species within the lower reproductive tract of the mammal. The *Porphyromonas* species can be *Porphyromonas somerae*. The *Porphyromonas* species can be the species having 16S rRNA that is greater than 98 percent identical to a 16 rRNA sequence of *Porphyromonas somerae*. The *Porphyromonas* species can be the species having 16S rRNA that is greater than 98.5 percent identical to a 16 rRNA sequence of *Porphyromonas somerae*. The FISH probe can comprise the sequence of SEQ ID NO:8 or SEQ ID NO:9.

In another aspect, this document features a method for identifying a female mammal as having endometrial cancer. The method comprises, or consists essentially of, (a) contacting a sample from the mammal with a FISH probe during a FISH technique to detect the presence of a *Porphyromonas* species within the upper reproductive tract of the mammal or the presence of an elevated level of the species within the lower reproductive tract of the mammal, wherein the species is *Porphyromonas somerae* or a species having 16S rRNA that is greater than 98 percent identical to a 16 rRNA sequence of *Porphyromonas somerae*, (b) contacting a sample from the mammal with PCR primers during an amplification reaction to detect the presence of the *Porphyromonas* species within the upper reproductive tract of the mammal or the presence of an elevated level of the species within the lower reproductive tract of the mammal, and (b) classifying the mammal as having endometrial cancer. The mammal can be a human. The method can comprise detecting the presence of the species within the upper reproductive tract of the mammal in the step (a) and the step (b). The method can comprise detecting the presence of the elevated level of the species within the lower reproductive tract of the mammal in the step (a) and the step (b). The *Porphyromonas* species can be *Porphyromonas* somerae. The *Porphyromonas* species can be the species having 16S rRNA that is greater than 98 percent identical to a 16 rRNA sequence of *Porphyromonas somerae*. The *Porphyromonas* species can be the species having 16S rRNA that is greater than 98.5 percent identical to a 16 rRNA sequence of *Porphyromonas somerae*. The FISH probe can comprise the sequence of SEQ ID NO:8 or SEQ ID NO:9. One of the PCR primers can comprise the sequence of SEQ ID NO:1 or SEQ ID NO:5.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
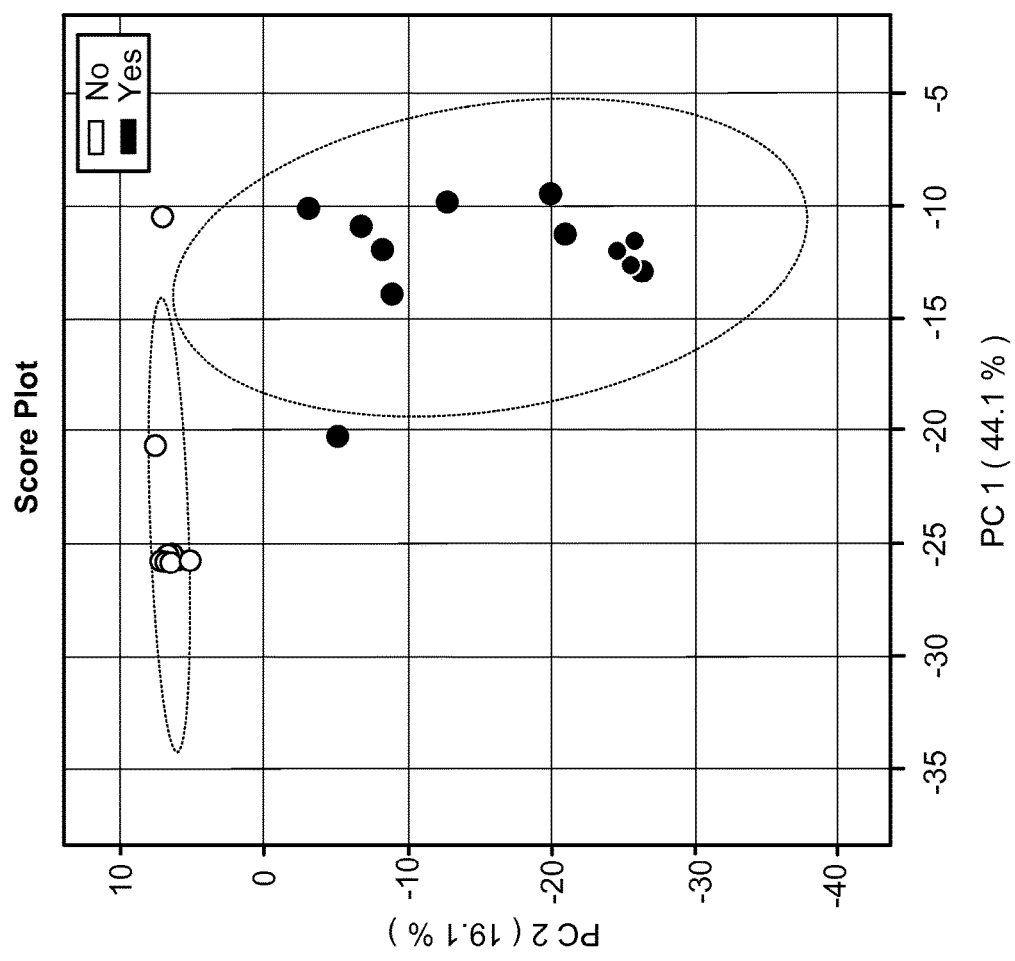
FIG. 1 is an ordination plot using principle coordinates analysis (PCA) to identify the relative clustering and differences between the uterine, vaginal, and cervical microbiomes of pre-menopausal (top elliptical region) and postmenopausal (larger elliptical region on right side of graph) women. The primary separation between these microbiomes is not driven by menopausal status. PCA with 95% Confidence Region.

This document provides methods and materials for treating endometrial cancer. For example, this document provides methods and materials for identifying a female mammal as having endometrial cancer and surgically removing at least the uterus of the female. As described herein, female mammals can be identified as having endometrial cancer at an early stage based at least in part on the presence of a Porphyromonas species in the upper reproductive tract and/or based at least in part on the presence of an elevated level of bacteria of a Porphyromonas species in the lower reproductive tract. The Porphyromonas species can be Porphyromonas somerae or a species having 16S rRNA that is greater than 98 percent identical (e.g., greater than 98 percent identical, greater than 98.5 percent identical, greater than 99 percent identical, or greater than 99.5 percent identical) to a 16 rRNA sequence of Porphyromonas somerae. A Porphyromonas somerae strain designated WAL 6690 is available from the ATCC® (ATCC® deposit number: BAA-1230™). See, also, Summanen et al., J. Clin. Microbiol., 43(9):4455 (2005)).

A reproductive tract sample can be an upper or lower reproductive tract sample. For example, an upper reproductive tract sample can be a sample obtained from a uterine swab, scrape, or biopsy. In some cases, an upper reproductive tract sample can be an endometrial, ovarian, fallopian tube, or peritoneal wash sample. A lower reproductive tract sample can be a sample obtained from a vaginal and/or cervical swab and scrape.

As described herein, detecting the presence of a Porphyromonas species within an upper reproductive tract sample can indicate that the female mammal has endometrial cancer, while detecting the presence of an elevated level of a Porphyromonas species within a lower reproductive tract sample can indicate that the female mammal has endometrial cancer. The term "elevated level" as used herein with respect to a level of a Porphyromonas species within a reproductive tract sample refers to any level that is greater than a reference level of a Porphyromonas species. The term "reference level" as used herein with respect to the level of a Porphyromonas species refers to the level of a Porphyromonas species typically observed in comparable reproductive tract samples from healthy female mammals without endometrial cancer. For example, a reference level of a Porphyromonas species can be the average number of Porphyromonas species present in reproductive tract samples obtained from a random sampling of 50 female humans free of endometrial cancer. In some cases, an elevated level of Porphyromonas species can be a level that is at least 10, 25, 50, 100, or 200 percent greater than a reference level of Porphyromonas species. In some cases, detecting the presence of an elevated level of a Porphyromonas species within an upper reproductive tract sample can indicate that the female mammal has endometrial cancer. In some cases, endometrial biopsies, dilatation and curettage procedures, transvaginal ultrasound examinations, or combinations thereof can be used to confirm that a female has endometrial cancer.

Any appropriate method can be used to detect the presence or amount of a Porphyromonas species within a reproductive tract sample. For example, PCR-based assays designed to amplify nucleic acid of a Porphyromonas species can be used to detect the presence or amount of a Porphyromonas species within a reproductive tract sample. In some cases, rRNA nucleic acid can be amplified and sequenced to detect the presence or amount of a Porphyromonas species within a reproductive tract sample.

In some cases, a PCR-based technique can be performed to amplify nucleic acid of a Porphyromonas species. Once amplified, the nucleic acid can be sequenced to confirm the presence of nucleic acid from a Porphyromonas species. In some cases, a pair of PCR primers or one or more probes specific for nucleic acid of a Porphyromonas species can be designed and used to detect the presence or amount of a Porphyromonas species within a sample with or without performing nucleic acid sequencing. For example, a PCR assay that includes a PCR primer pair designed to amplify nucleic acid of a Porphyromonas species and not nucleic acid from other species can be used to detect the presence or amount of a Porphyromonas species within a sample.

In some cases, fluorescence in situ hybridization (FISH) can be performed to detect the presence or amount of a Porphyromonas species within a sample. For example, FISH can be performed using one or more FISH probes designed to hybridize to nucleic acid of a Porphyromonas species. Such a FISH technique can be used to detect the presence or amount of a Porphyromonas species within a sample.

In some cases, a reproductive tract sample can be assessed using both a PCR-based technique and a FISH technique. In such cases, those samples where both the PCR-based technique and the FISH technique revealed the presence of a Porphyromonas species can be identified or classified as containing a Porphyromonas species, while those samples where both the PCR-based technique and the FISH technique revealed the absence of a Porphyromonas species can be identified or classified as lacking a Porphyromonas species. In those cases where only one of the two techniques revealed the presence of a Porphyromonas species, the sample can be re-assessed and/or further analysis can be performed (e.g., sequencing).

Once identified as having endometrial cancer based at least in part on the presence of a Porphyromonas species in the upper reproductive tract and/or an elevated level of a Porphyromonas species in the lower reproductive tract as described herein, at least the uterus of the female mammal can be surgically removed. For example, a female mammal identified as having endometrial cancer as described herein can be treated by performing a total hysterectomy (e.g., a vaginal hysterectomy, an abdominal hysterectomy, a total laparoscopic hysterectomy, a total hysterectomy with lateral or bilateral salpingo-oophorectomy, or a radical hysterectomy). In some cases, a female mammal identified as having endometrial cancer as described herein can be treated using radiation therapy (e.g., high-energy x-ray therapy), chemotherapy (e.g., paclitaxel, carboplatin, doxorubicin, and/or cisplatin therapy), or hormone therapy (e.g., tamoxifen, goserelin, leuprolide, exemestane, anastrozole, and/or letrozole therapy) in combination with or in place of surgery.

In some cases, a female mammal having endometrial cancer and the presence of a *Porphyromonas* species in the upper reproductive tract and/or an elevated level of a *Porphyromonas* species in the lower reproductive tract can be treated with one or more agents (e.g., antibiotics) having the ability to kill *Porphyromonas* species. For example, a female mammal identified as having endometrial cancer as described herein can be treated by administering an antibiotic to the mammal under conditions wherein the number of *Porphyromonas* species bacteria present within the upper reproductive tract and/or lower reproductive tract is reduced.

In some cases, a female mammal having a likelihood of developing endometrial cancer and having a *Porphyromonas* species in the upper reproductive tract and/or an elevated level of a *Porphyromonas* species in the lower reproductive tract can be treated with one or more agents (e.g., antibiotics) having the ability to kill *Porphyromonas* species. For example, a female mammal identified as having a *Porphyromonas* species in the upper reproductive tract can be treated by administering an antibiotic to the mammal under conditions wherein the number of *Porphyromonas* species bacteria present within the upper reproductive tract is reduced. Examples of antibiotics that can be used to treat a female mammal as described herein include, without limitation, benzylpenicillin, tetracycline, amoxicillin, ampicillin, ticarcillin, piperacillin, cephalothin, cefuroxime, cefotaxime, cefoxitin, imipenem erythromycin, cefamandole, cephaloridine, oleandomycin, metronidazole, spiramycin, and clindamycin.

The invention will be further described in the following examples, which do not limit the scope of the invention described in the claims.

EXAMPLES

Example 1—Presence of Elevated Level of *Porphyromonas* Species in the Reproductive Tract Indicates the Presence of Endometrial Cancer Subject Enrollment 16 human subjects were enrolled in this study. The inclusion criteria were the following: 18 years of age or older; females undergoing hysterectomy by any standard surgical approach; and undergoing hysterectomy for benign disease, hyperplasia, or any stage of endometrial cancer. Patients with any of the following criteria were excluded from this study: women who were pregnant or nursing; women who took antibiotics within two weeks preceding surgery; and women where the surgeon anticipates the use of a morcellator during the hysterectomy procedure due to the size of the uterus or for any other reason. Upon enrollment, the subjects were requested to fill out an optional questionnaire about sexual and reproductive health and history. The metadata from the questionnaires were stored at REDCap (Harris et al., *J. Biomed. Inform.*, 42:377-81 (2009)).

Vaginal and Cervical Sample Collection

All subjects were requested not to douche with betadine on the surgery day or the day immediately preceding it. The vaginal and cervical swabs and scrapes were collected by the surgeon with guidance on site by the research team immediately after the administration of anesthesia and immediately preceding the standard pre-surgical betadine douche. Both the vaginal and cervical swabs were performed with three sterile Dacron swabs each and placed in a sterile tube with 1 mL of Tris-EDTA (TE) buffer kept on dry ice until storage at −80° C. One of the vaginal swabs was used for immediate on-site vaginal pH measurement with a Hydrion measuring pH tape. The scrapes were performed using sterilized (autoclaved at 121° C. for 20 minutes) pap smear spatulas and placed in sterile tubes with TE buffer kept in dry ice until storage.

Uterine, Fallopian, and Ovarian Sample Collection

Once removed, the uterus, fallopian tubes, and ovaries were handed by the surgeon to the instrumentalist nurse who placed them inside a sterile transport bag and into a closed sterile container. The container was transported to the pathology lab (within the same clean area), where the organs were handed to a pathology assistant (PA) who processed them under sterile conditions. The grossing station where the specimen was processed was sterilized by the research team, including all tools needed by the PA for handling. The PA used surgical gloves and mask when handling the specimen. The PA performed a bilateral cut of the uterus and splayed it. If the uterus belonged to a non-cancer subject, then the research team advanced to the collection of the uterine swabs (Dacron) and scrapes (sterilized pap smear spatulas) and documentation (by placement of push pins in sampled locations and digital photograph. The PA then proceeded to the aseptic collection of samples needed for the diagnosis, and once complete, the research team collected the uterine, fallopian, and ovarian biopsies (approximately 4 mm of tissue was collected per biopsy by the use of a sterile tweezers, scalpels, and surgical ruler). If the uterus belonged to a cancer subject, the collection of the swabs and scrapes was performed after the complete diagnostic procedures so as to avoid delay in the cancer staging determination, which can impact in the progression of the surgery in the operating room. Each collected sample was placed in a sterile tube with 1 mL of TE buffer and kept on dry ice until storage at −80° C. A petri dish with LB was kept open on the grossing station during sample collection to detect any possible airborne contamination of the specimen. The LB was swabbed, and the swab was stored in a tube with 1 mL of TE and kept on dry ice until storage along with the other samples.

Sample Processing

Once thawed, the swab and scrape samples were vortexed to bring the collected material into solution. The biopsy samples were mushed by the use of sterile pestles. The swab and scrape samples were centrifuged for 10 minutes at 10,000 g to collect the bacterial cells, and the supernatant was discarded. All genomic DNA extractions were performed by using the MoBio PowerSoil Kit (MoBio Laboratories, Inc., Carlsbad, Calif.); however, instead of vortexing, MP FastPrep (MP Biomedicals, Solon, Ohio) was used for 60 seconds at 6.0 m/s to obtain a more effective and rapid lysis of the cells. The incubation period was for a minimum of 30 minutes and a maximum of overnight. After extraction, the DNA content was measured using High Sensitivity Qubit (Life Technologies Corporation, Carlsbad, Calif.). The V3-V5 region of the 16S rDNA was then amplified through a polymerase chain reaction (PCR) as follows: 25 µL of Kapa HiFi (Kapa Biosystems, Woburn, Mass.), 1.5 μL (10 μM) forward primer, 1.5 μL (10 μM) reverse primer, 50 ng of DNA with the remaining volume being added by molecular grade water (up to a final volume of 50 μL per reaction). The forward primer was the universal primer 357F (5'-GTCCTACGGGAGGCAGCAG-3'; SEQ ID NO:1) with the added construct on the 5' end of the 5' Illumina Adapter (5'-AATGATACGGCGAC-CACCGAGATCTACAC-3'; SEQ ID NO:2)+Forward Primer Pad (5'-TATGGT-AATT-3'; SEQ ID NO:3) to a total sequence: 5'-AATGATACGGC-GACCACCGA-GATCTACACTATGGTAATTGTC-CTACGGGAGGCAGCAG-3' (SEQ ID NO:4), and the universal bacterial reverse primer was 926R (5'-CCGTCAATTCMTTTRAGT-3'; SEQ ID NO:5) with an added construct on the 5' end of the reverse complement of 3' Illumina adapter (5'-CAAGCAGAAGACGGCATACGA-GATGCCGCATTCGAT-3'; SEQ ID NO:6)+Barcode (12 base pairs) to a total sequence: 5'-CAAGCAGAAG-ACG-GCATACGAGATGCCGCATTC-GATXXXXXXXXXXXXCCGTCAATTCMTTT RAGT-3' (SEQ ID NO:7). The barcode introduced in the reverse primer construct was unique to each sample, functioning as a genetic ID for sequencing. The PCR cycle was the following: 95° C. for 3 minutes, 98° C. for 20 seconds, 70° C. for 15 seconds, 72° C. for 15 seconds; cycle repeated for 34 times and 72° C. for 5 minutes. The products of the amplification were verified by TapeStation D1K Tape (2200 TapeStation Instrument, Agilent Technologies, Santa Clara, Calif.) to be free of contamination and the expected amplification size (approximately 700 base pairs). If the amplification was unsuccessful, the parameters of the reaction or cycle were adjusted in repeated attempts. In some cases (mostly biopsy samples), the amplification was not successful even after repeated attempts. The reduced number of microorganisms present in the upper reproductive tract was likely to justify this result and attests for the success of the sterile collection of the samples. Upon verification, the PCR products were purified using Agencourt AMPure (Beckman Coulter, Brea, Calif.). After purification, the concentrations were measured using Qubit High Sensitivity. The 16S sequencing was performed by the MGF (Medical Genome facility at Mayo Clinic, Rochester) using a high-throughput next-generation Illumina MiSeq (San Diego, Calif.) sequencing platform.

Sequence Analysis

Sequence reads were aligned with an alignment tool that merges paired end reads into a single multiple alignment and obtains taxa calls (Sipos et al., *PLoS One*, 5:e15220 (2010)). IM-TORNADO then clustered sequences into operational taxonomic units (OTUs) using AbundantOTU+ (Ye, *Proceedings IEEE Int. Conf Bioinformatics Biomed*, 2010: 153-7 (2011)).

Sequencing Outcome

A total of 16,366,472 sequence reads (17,657 to 828,181 reads per sample) were obtained (mean of 199,591±190,153 reads) after quality control. Further processing for visualization was performed using QIIME (Caporaso et al., Nat. Methods, 7:335-6 (2010)) and METAGENassist (Arndt et al., *Nucleic Acids Research*, 40(Web Server issue):W88-95 (2012)).

Results

Results were obtained from 16 subjects: six with a benign diagnosis (including two with a diagnosis of menorrhagia, a risk factor for the development of endometrial cancer) and ten with biopsy proven endometrial cancer (Grade I-III). Ethnicity and age were not targeted, with all the enrolled subjects being Caucasian and a mean age of 59±9 (51±9 years old for the benign subjects, and 67±8 years old for the cancer subjects). The benign cohort had 40% post-menopausal women, while the cancer cohort had 80% post-menopausal women. All subjects were asked to fill an optional gynecologic health and sexual history questionnaire. Of the benign subjects, 60% had previously undergone a gynecologic surgery (tubal ligation being the most common) with only 33% of the cancer subjects having had any previous gynecologic surgery. Benign subjects self-reported an average of 5±3 sexual partners, while cancer subjects reported 1±0. The majority (63%) of the subjects self-reported incontinence (60% for benign subjects, and 67% for cancer subjects).

The effect of menopausal status on the microbial populations was examined in the uterus. Menopausal status was self-reported and confirmed by the measurement of the vaginal pH at the time of sample collection. All self-reported post-menopausal patients had a vaginal pH>4.5. Of the 16 enrolled patients, 11 were post-menopausal. Menopausal status significantly impacted the microbiome in both the lower and upper reproductive tract (FIG. 1). A particular microorganism, with 90% sequence similarity to *Barnesiella intestinihominis* was found significantly higher in postmenopausal women throughout the reproductive tract. A variety of other microorganisms, commonly associated with the gastrointestinal tract were also detected at significantly different proportions between the two groups of women (Table 1).

TABLE 1

Significant differences found between the frequencies of the OTUs (Operational Taxonomic Unites) in postmenopausal women when compared to premenopausal women. Generated by Kruskal-Wallis analysis with 1,000 permutations through QIIME.

| OTU | p-value | Bonferroni Correction | Post-Menopause Mean | Pre-Menopause Mean | Taxonomy |
|---|---|---|---|---|---|
| | | | Uterus | | |
| 20 | 2.58E−06 | 0.001938339 | 6280 | 0 | Bacteroidetes; Barnesiella; B. intestinihominis (90% identity) |
| 469 | 2.58E−06 | 0.001938339 | 510 | 0 | Firmicutes; Clostridium; C. sp. (99% identity) |
| 16 | 5.06E−06 | 0.003798545 | 12319 | 62 | Bacteroidetes; Barnesiella; B. intestinihominis (90% identity) |

TABLE 1-continued

Significant differences found between the frequencies of the OTUs (Operational Taxonomic Unites) in postmenopausal women when compared to premenopausal women. Generated by Kruskal-Wallis analysis with 1,000 permutations through QIIME.

| OTU | p-value | Bonferroni Correction | Post-Menopause Mean | Pre-Menopause Mean | Taxonomy |
|---|---|---|---|---|---|
| 41 | 7.03E−06 | 0.005280118 | 0.3 | 1045 | Proteobacteria; Pseudomonas; P. aeruginosa (100% identity) |
| 36 | 1.06E−05 | 0.007964362 | 1532 | 0 | Firmicutes; Oscillospira; O. guilliermondii (97% identity) |
| 24 | 1.06E−05 | 0.007964362 | 2653 | 0 | Bacteroidetes; Barnesiella; B. intestinihominis (89% identity) |
| 11 | 1.10E−05 | 0.008225203 | 8268 | 84 | Bacteroidetes; Bacteroides; B. acidifaciens (100% identity) |
| Lower Reproductive Tract | | | | | |
| 16 | 6.31E−06 | 0.004740987 | 4228 | 12 | Bacteroidetes; Barnesiella; B. intestinihominis (90% identity) |
| 90 | 9.23E−06 | 0.00693405 | 0 | 145 | Firmicutes; Lactobacillus; L. delbrueckii (100% identity) |

Figure 2:
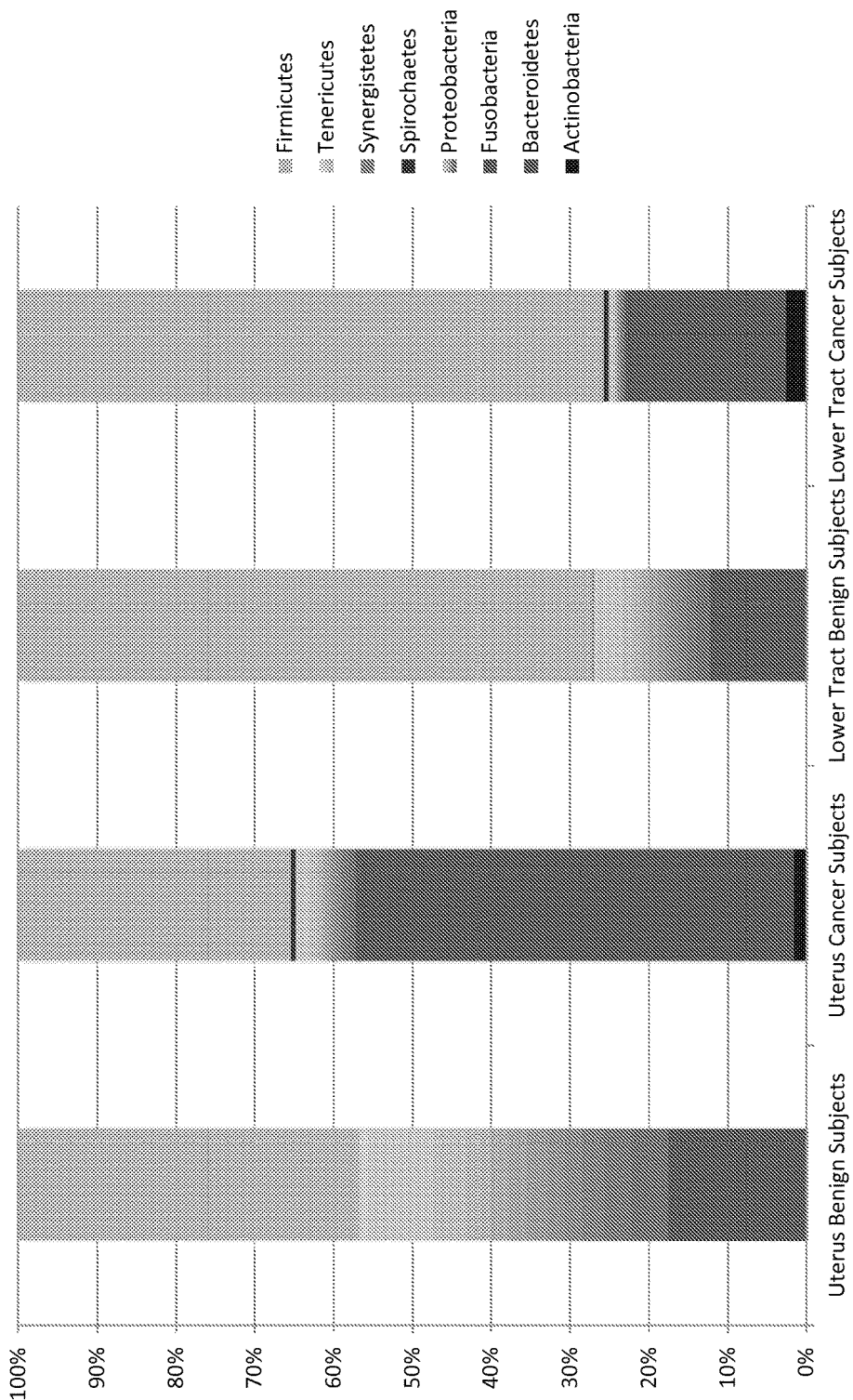
FIG. 2 is a bar graph presenting the microbiome at the phylum level by abundance in the indicated samples. Statistical differences between the cancer and benign microbiomes in the upper and lower reproductive tracts was calculated using permanova with 999 permutations and resulted in pseudo-F=0.007 and pseudo-F=0.008, respectively.

The samples collected from non-cancer (6 subjects) and cancer (10 subjects) participants were analyzed and compared (FIG. 2). A decreased abundance of Proteobacteria and an increased abundance of Bacteroidetes and Actinobacteria were found in the samples from the uterine cavity of cancer subjects when compared to samples collected from non-cancer subjects (FIG. 2). This trend also was observed in the samples collected from the lower reproductive tract (vagina and cervix).

Figure 3:
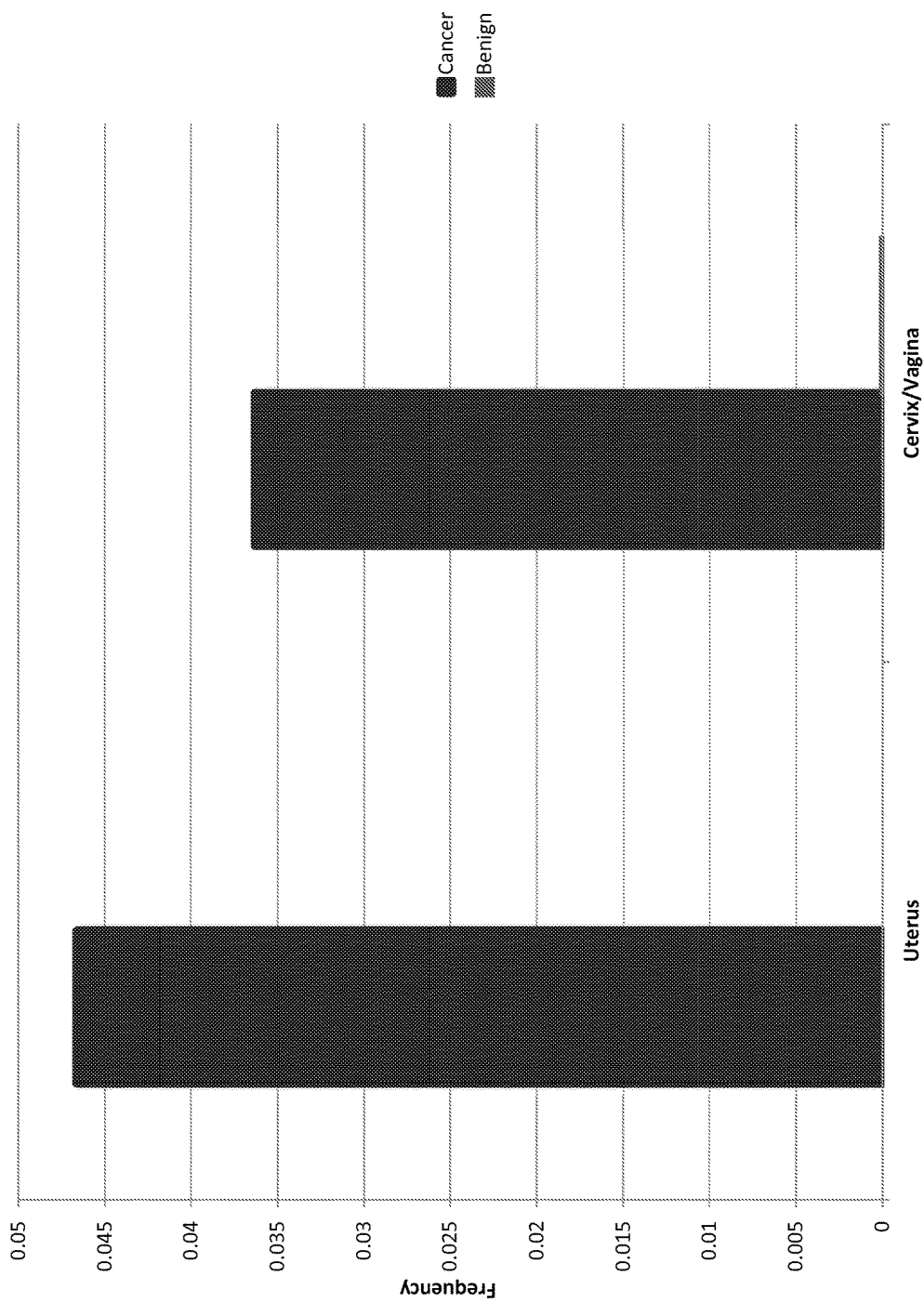
FIG. 3 shows the relative abundance of Porphyromonas sp. in cancer and benign cases in both upper and lower reproductive tracts. Statistical testing using the Kruskal-Wallis test with 1000 permutations results in high significance for cancer detection: Uterus Cancer vs. Benign: p-value: 8.55E−7 (FDR: 6.42E−4; Bonferroni: 6.42E−4). Cervix/Vagina Cancer vs. Benign: p-value: 2.02E−6 (FDR: 1.52E−3; Bonferroni: 1.52E−3).

A particular *Porphyromonas* sp. having about 99% identity to *Porphyromonas somerae* was exclusively collected from the upper reproductive tract of cancer subjects (FIG. 3). All sequenced samples (9 samples from 5 cancer subjects) from the upper reproductive tract of cancer subjects were positive for this microorganism, including samples collected from the Fallopian tubes and stool samples. By contrast, all sequenced samples (25 samples from 5 benign subjects) from the upper reproductive tract of non-cancer subjects were negative for this microorganism, including samples collected from the Fallopian tubes (including a cyst sample) and ovaries.

Figure 4:
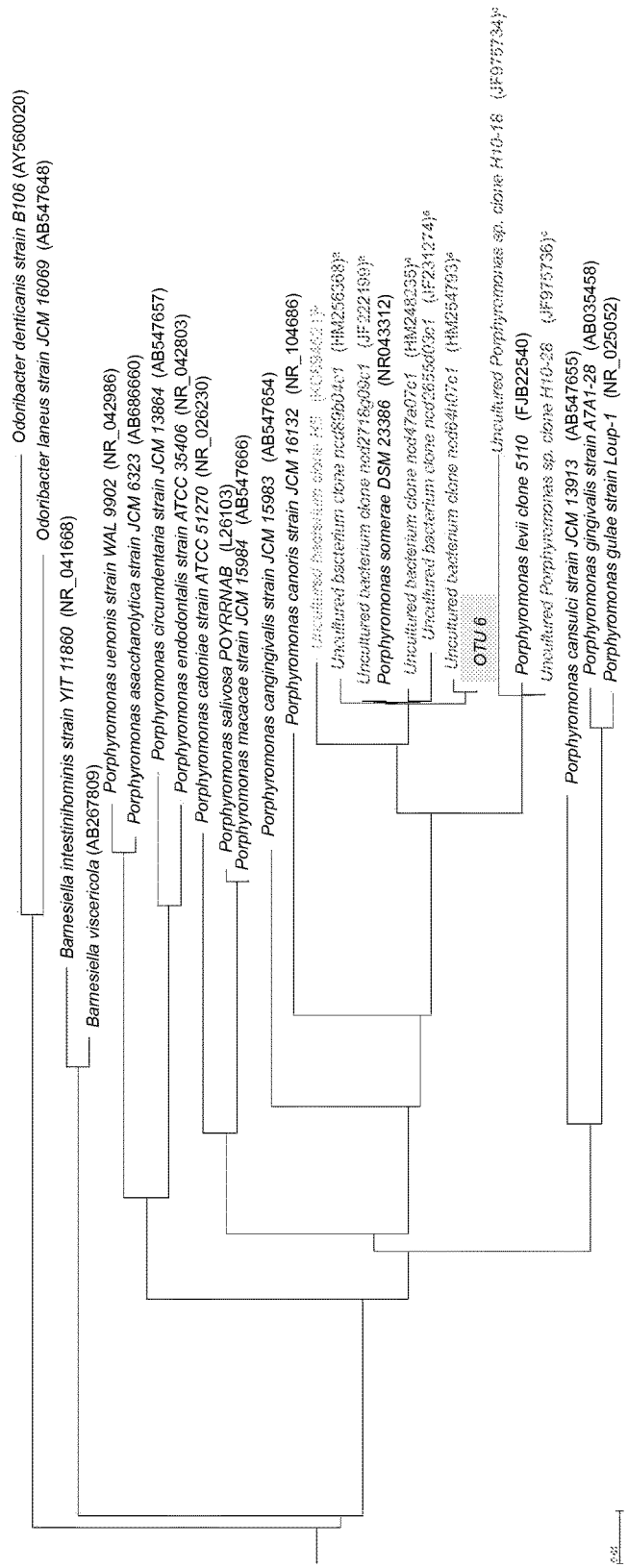
FIG. 4 is a maximum likelihood phylogenetic tree of V3-V5 16S rDNA region. $^a$Recovered from children with atopic dermatitis (Kong et al., Genome Research, 22(5), 850-859 (2012)); $^b$Recovered from buffaloes with postpartum endometritis; $^c$Recovered from Holstein dairy cows with postpartum metritis (Peng et al., Folia microbiologica, 58(6):593-600 (2013)). Produced with FASTTREE.

A phylogenetic analysis confirmed the close affiliation of the microorganism recovered with *Porphyromonas somerae* and other uncultured *Porphyromonas* species recovered from children with atopic dermatitis (Kong et al., *Genome Research*, 22(5), 850-859 (2012)) and buffaloes with postpartum endometritis (Peng et al., *Folia microbiologica*, 58(6):593-600 (2013)) (FIG. 4). The phylogeny also revealed that the second closest cultured representative was *Porphyromonas levii* (96% sequence identity).

This *Porphyromonas* sp. microorganism also was found in significantly higher abundance (e.g., >100 times greater abundance) in the lower reproductive tract of cancer subjects (25 samples, 9 subjects) than in non-cancer subjects (20 samples, 6 subjects) (FIG. 3).

Example 2—Treating Endometrial Cancer

An upper or lower reproductive tract sample is obtained from a female human, who is between about 25 and about 80 years old (e.g., between about 30 and about 65 years old, between about 35 and about 60 years old, or between about 40 and about 55 years old) and who lacks symptoms of endometrial cancer as observable from a routine physical examination. The obtained sample is examined for the presence of and/or amount of a *Porphyromonas* species such as *Porphyromonas somerae* or a *Porphyromonas* species having greater than 98 percent identity (e.g., greater than 99 percent identity) to *Porphyromonas somerae*. In some cases, a PCR-based assay is performed to detect the presence of or amount of such a *Porphyromonas* species. If a *Porphyromonas* species such as *Porphyromonas somerae* or a *Porphyromonas* species having greater than 98 percent identity (e.g., greater than 99 percent identity) to *Porphyromonas somerae* is detected in an upper reproductive tract sample or if an elevated level of such a *Porphyromonas* species is detected in a lower reproductive tract sample, then the female human is treated by performing a total hysterectomy (e.g., a vaginal hysterectomy, an abdominal hysterectomy, a total laparoscopic hysterectomy, a total hysterectomy with lateral or bilateral salpingo-oophorectomy, or a radical hysterectomy). Optionally, an endometrial biopsy, dilatation and curettage procedure, transvaginal ultrasound examination, or a combination thereof is performed prior to the hysterectomy to confirm that the female human has endometrial cancer.

Example 3—Using FISH to Detect a *Porphyromonas* Species Within Tissue Samples

Frozen tissue sections and/or liquid culture sections are pretreated by allowing the sections to air dry for 30 minutes at room temperature. The sections are fixed in 4% paraformaldehyde for 15 minutes at room temperature and washed three times for 5 minutes each in PBS. The sections are incubated in 0.15% $H_2O_2$ in PBS for 30 minutes, and the slides are equilibrated in 4×SSC for 15 minutes.

Hybridization is performed in a humidity chamber. The humidity chamber is prepared with a hybridization box or tube with a formamide/water mixture. The sections are covered with hybridization buffer, and the slides are inserted into a preheated humidity chamber. After incubating the slides for 20 minutes at 37° C., the buffer is removed, and a hybridization buffer mixed with a probe working solution (50 ng DNA/μL in a ratio of 100:1 is applied to the sections. The probe is either 5'-CAG-CCAAGTCGCGTGAAGGA-3' (SEQ ID NO:8) or 5'-AGGATAGGTACGTGTACC-TATTAGA-3' (SEQ ID NO:9) with horseradish peroxidase (HRP) attached at the 5' end. For each section, 500 μL is sufficient. The sections are incubated overnight at 37° C.

A washing step is performed by removing the hybridization buffer by dabbing the slide onto tissue. The slides are then dipped in the first washing buffer followed by a second washing buffer for 15 minutes at 37° C. The slides are incubated in 1×PBS (pH 8) under shaking conditions at room temperature for 15 minutes to 1 hour.

A humidity chamber is prepared by inserting the tissue to the bottom of 50 mL tubes and soaking them with water. A fresh solution of $H_2O_2$ (0.15% in PBS) is prepared and kept cool. An amplification buffer is mixed with the peroxide solution 100:1 and fluorescently labeled tyramide (1 mg dye/mL) and is kept in the dark.

The amplification mix is applied onto the sections, which are incubated at 37° C. for 20 minutes in a humidity chamber. Excess liquid is removed and incubated in 1×PBS for 15 minutes at room temperature in the dark. The slides are washed with water and allowed to air dry before being counterstained with DAPI.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for treating a female mammal having endometrial cancer, wherein said method comprises:
    (a) identifying said mammal as having a *Porphyromonas* species within the upper reproductive tract of said mammal or as having an elevated level of said species within the lower reproductive tract of said mammal, wherein said species is *Porphyromonas somerae* or a species having 16S rRNA that is greater than 98 percent identical to a 16 rRNA sequence of *Porphyromonas somerae*, and
    (b) administering an antibiotic to said mammal to reduce the number of said species within said mammal.

2. The method of claim 1, wherein said mammal is a human.

3. The method of claim 1, wherein said method comprises identifying said mammal as having said species within the upper reproductive tract of said mammal.

4. The method of claim 1, wherein said method comprises identifying said mammal as having said elevated level of said species within the lower reproductive tract of said mammal.

5. The method of claim 1, wherein said *Porphyromonas* species is *Porphyromonas somerae*.

6. The method of claim 1, wherein said *Porphyromonas* species is said species having 16S rRNA that is greater than 98 percent identical to a 16 rRNA sequence of *Porphyromonas somerae*.

7. The method of claim 1, wherein said *Porphyromonas* species is said species having 16S rRNA that is greater than 98.5 percent identical to a 16 rRNA sequence of *Porphyromonas somerae*.

8. The method of claim 1, wherein said antibiotic is benzylpenicillin, tetracycline, amoxicillin, ampicillin, ticarcillin, piperacillin, cephalothin, cefuroxime, cefotaxime, cefoxitin, imipenem erythromycin, cefamandole, cephaloridine, oleandomycin, metronidazole, spiramycin, or clindamycin.

* * * * *

SEQUENCE LISTING

```
<160> NUMBER OF SEQ ID NOS: 9

<210> SEQ ID NO 1
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 1
gtcctacggg aggcagcag                                                19

<210> SEQ ID NO 2
<211> LENGTH: 29
<212> TYPE: DNA
<213> ORGANISM: Artificial Sequence
<220> FEATURE:
<223> OTHER INFORMATION: synthetic oligonucleotide

<400> SEQUENCE: 2
aatgatacgg cgaccaccga gatctacac                                      29

<210> SEQ ID NO 3
<211> LENGTH: 10
<212> TYPE: DNA
<213> ORGANISM: Artificial Sequence
<220> FEATURE:
<223> OTHER INFORMATION: synthetic oligonucleotide

<400> SEQUENCE: 3
tatggtaatt                                                          10

<210> SEQ ID NO 4
<211> LENGTH: 58
<212> TYPE: DNA
<213> ORGANISM: Artificial Sequence
<220> FEATURE:
<223> OTHER INFORMATION: synthetic oligonucleotide

<400> SEQUENCE: 4
aatgatacgg cgaccaccga gatctacact atggtaattg tcctacggga ggcagcag     58
```

<210> SEQ ID NO 5
<211> LENGTH: 18
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (11)...(11)
<223> OTHER INFORMATION: n = a or c
<220> FEATURE:
<221> NAME/KEY: misc_feature
<222> LOCATION: (15)...(15)
<223> OTHER INFORMATION: n = a or g

<400> SEQUENCE: 5
ccgtcaattc ntttnagt                                            18

<210> SEQ ID NO 6
<211> LENGTH: 36
<212> TYPE: DNA
<213> ORGANISM: Artificial Sequence
<220> FEATURE:
<223> OTHER INFORMATION: synthetic oligonucleotide

<400> SEQUENCE: 6
caagcagaag acggcatacg agatgccgca ttcgat                        36

<210> SEQ ID NO 7
<211> LENGTH: 66
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (37)...(48)
<223> OTHER INFORMATION: n = a, t, g or c
<220> FEATURE:
<221> NAME/KEY: misc_feature
<222> LOCATION: (59)...(59)
<223> OTHER INFORMATION: n = a or c
<220> FEATURE:
<221> NAME/KEY: misc_feature
<222> LOCATION: (63)...(63)
<223> OTHER INFORMATION: n = a or g

<400> SEQUENCE: 7
caagcagaag acggcatacg agatgccgca ttcgatnnnn nnnnnnncc gtcaattcnt    60 ttnagt                                                             66

<210> SEQ ID NO 8
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 8
cagccaagtc gcgtgaagga                                          20

<210> SEQ ID NO 9
<211> LENGTH: 25
<212> TYPE: DNA
<213> ORGANISM: Artificial Sequence
<220> FEATURE:
<223> OTHER INFORMATION: synthetic oligonucleotide -continued

```
<400> SEQUENCE: 9
aggataggta cgtgtaccta ttaga                                              25
```